United States Patent [19]

Pohl

[11] Patent Number: 4,476,004
[45] Date of Patent: Oct. 9, 1984

[54] APPARATUS FOR ELECTROFUSION OF BIOLOGICAL PARTICLES

[75] Inventor: Herbert A. Pohl, Stillwater, Okla.

[73] Assignee: D.E.P. Systems, Inc., Metamora, Mich.

[21] Appl. No.: 545,751

[22] Filed: Oct. 26, 1983

Related U.S. Application Data

[63] Continuation of Ser. No. 483,290, Apr. 8, 1983, Pat. No. 4,441,972.

[51] Int. Cl.$^3$ ............................................. B01D 57/02
[52] U.S. Cl. ............................... 204/299 R; 204/302
[58] Field of Search ............... 204/299 R, 180 R, 186, 204/302

[56] References Cited

U.S. PATENT DOCUMENTS 3,162,592 12/1964 Pohl .................................... 204/186
4,326,934 4/1982 Pohl ................................. 204/180 R

OTHER PUBLICATIONS

Zimmermann, U., et al, "Fusion of Avena Sativa Mesophyll Gell Protoplasts by Electrical Breakdown", *Biochimica et Biophysica Acta*, 641, (1981), 160–165.
Pohl, H. A., et al, "The Continuous Positive and Negative Dielectrophoresis of Microorganisms", *J. Bio. Phys.*, 9, 67–86, (1981).
Zimmermann, U., et al, "Electric Field-Induced Cell-To-Cell Fusion", *J. Membrane Biol.*, 67, 165–182, (1982).
Vienken, J., et al, "Electric Field-Induced Fusion: Electro-Hydraulic Procedure for Production of Heterokaryon Cells in High Yield", *Fed. Eur. Biomed. Soc. Lett.*, 137, 11–13, (1982).
Crane, J. S., et al, "Use of the Balanced-Cell Technique to Determine Properties of Single Yeast Cells", *J. Biol. Phys.*, 5, 49–73, (1978).
Bischoff, et al, "Human Hybridoma Cells Produced by Electro-Fusion", *Fed. Eur. Biochem. Soc. Lett.*, 147, 64–68, (1982).
Halfmann, H. H., et al, "Transfer of Mitochondrial Function into a Cytoplasmic Respiratory-Deficient Mutant of Saccharomyces Yeast by Electro-Fusion", *Current Genetics*, 6, 25–28, (1982).
Hub, H. H., et al, "Preparation of Large Unilamellar Vesicles", *Fed. Eur. Biochem. Soc. Lett.*, 140, 254–256, (1982).
Zimmermann, U., et al, "Electric Field-Induced Release of Chloroplasts from Plant Protoplasts", *Naturwissen*, 69, 451, (1982).
Zimmermann, U., et al, "Electric Field-Mediated Cell Fusion", *J. Biol. Phys*, 10, 43–50, (1982).
Changben, L., et al, "Use of Human Erythrocyte Ghosts for Transfer of $^{125}$I–BSA and $^{125}$I–DNA into Animal Cells from Cell Fusion", *Scientia Sinica (Series B)*, 25, 680–865, (1982).
Neumann, B., et al, "Cell Fusion Induced by High Electrical Impulses Applied to Dictyostelium", *Naturissen*, 67, 414, (1980).
Murch, A. R., et al, "Direct Evidence That Inflammatory Multinucleate Giant Cells Form by Fusion", *Pathol. Soc. Gr. Brit. Ire.*, 137, 177–180, (1982).
Zimmermann, U., "Cells with Manipulated Functions: New Perspectives for Cell Biology, Medicine, and Technology", *Angew, Chem. Int. Ed. Engl.*, 20, 325–344, (1981).
Chen, C. S., et al, "Biological Dielectrophoresis: The Behavior of Lone Cells in a Nonuniform Electric Field", *Ann. N.Y. Acad. Sci.*, 238, 176–185, (1974).

(List continued on next page.)

Primary Examiner—John F. Niebling
Assistant Examiner—B. J. Boggs, Jr.
Attorney, Agent, or Firm—Flehr, Hohbach, Test, Albritton & Herbert

[57] ABSTRACT

Apparatus and methods of use thereof are provided for fusing neutral polarizable biological bodies and sorting neutral polarizable biological bodies by imposing them to a non-uniform electric field. The dielectrophoretic effect of the non-uniform electric field will either impose variable displacements of the types of cells to facilitate sorting, or will align cells contiguously between a pair of electrodes in preparation for fusion. To fuse the cells the aligned cells are exposed to a direct current impulse.

4 Claims, 8 Drawing Figures

OTHER PUBLICATIONS

Kaler, K., et al, "Dynamic Dielectrophoretic Levitation of Living Individual Cells", *J. Biol. Phys.*, 8, 18–31, (1980).

Weber, H., et al, "Enhancement of Yeast Protoplast Fusion by Electric Field Effects", a preprint for *Proceedings of the Fifth International Symposium on Yeasts, London,* Ontario, Canada, (Jul. 1980).

Pohl, H. A., et al, "Continuous Dielectrophoretic Separation of Cell Mixtures", *Cell Biophys.*, 1, 15–28, (1979).

Pohl, H. A., et al, "Dielectrophoretic Force", *J. Biol. Phys.*, 6, 133, (1978).

Pohl, H. A., "Biophysical Aspects of Dielectrophoresis", *J. Biol. Phys.*, 1, 1–16, (1973).

APPARATUS FOR ELECTROFUSION OF BIOLOGICAL PARTICLES

This is a continuation, of application Ser. No. 483,290 filed on Apr. 8, 1983, now U.S. Pat. No. 4,441,972.

The present invention is directed to apparatus for fusing biological particles by electrical means. The present invention is further directed to apparatus for sorting biological particles by the application of non-uniform electric fields to such particles.

The apparatus according to the present invention may be utilized to fuse biological particles by the process of electrofusion or to sort biological particles by the process of dielectrophoresis. The process of electrofusion involves exposing the biological particles, such as cells, which are to be fused to a mild non-uniform electrical field to align the cells between inert electrodes. Typically, a mild alternating current field of about 10 volts rms at about 250 khz may be utilized. After alignment, a short pulse of about 15 volts dc for about 50 microseconds may be applied, which causes a dielectric breakdown of the contiguous cell membranes, thereby opening a membrane channel between the cell interiors of contiguous cells. The cells then fuse together. Using electrofusion, fusion yields of over 25%, and often approaching 100%, may be readily obtainable, as compared to about 0.001% to 5% efficiency for classical methods of cell fusion, such as, treatment with virus particles or polyethylene glycol. A major advantage of electrofusion is in its provision of a precise time of the onset of fusion-related events, which may be important in the rate studies of fusion-related events in cells in the fields of genetics, morphology, cell surfaces, and cell physiology.

The exposure of neutral particles, particularly biological particles such as cells, to non-uniform electric fields induces a dipole in each particle. If dc current is not applied to fuse the cells, then the divergent non-uniform nature of the field results in one end of the dipole being in a region of higher field strength than the other and this effect causes the dipole to be pulled in the direction of the increasing field. Therefore, non-uniform electric fields can induce translational and rotational motion of biological particles in suspension. This motion has been defined as dielectrophoresis. These motions can be used to characterize and separate biological particles, such as living cells and parts thereof. Apparatus utilizing the dielectrophoresis phenomenon are described in my U.S. Pat. Nos. 3,162,592 and 4,326,934.

It is therefore an object of the present invention to provide improved apparatus for electrofusion of cells which are convenient, versatile and adaptable for handling a high number of biological particles per unit time.

It is a further object of the present invention to provide apparatus for sorting cells by dielectrophoresis which may handle a large number of cells per unit time.

These and other objects will become readily apparent from the following description and claims.

One embodiment of the present invention comprises a disk chamber which includes a set of parallel electrodes at least one of which is provided with concentric circular grooves. When the electrodes are spaced apart and supplied with an ac voltage the sharp edges of the grooves provide a non-uniform electric field. This field may either be used to align cells in preparation for later fusion by a dc (or ac) pulse or may be used to sort and characterize biological cells by dielectrophoresis. The dielectrophoresis sorting technique may be used, for example, to distinguish biological particles such as cells by age, abnormalities, history and culture media, hemophilic traits, and the like. Dielectrophoresis may also be utilized to separate mixtures of biological cells by type or by physiological condition. The disk chamber according to the present invention may be advantageously used to sort biological cells with the rates up to about 10 million cells per minute.

Figure 1:
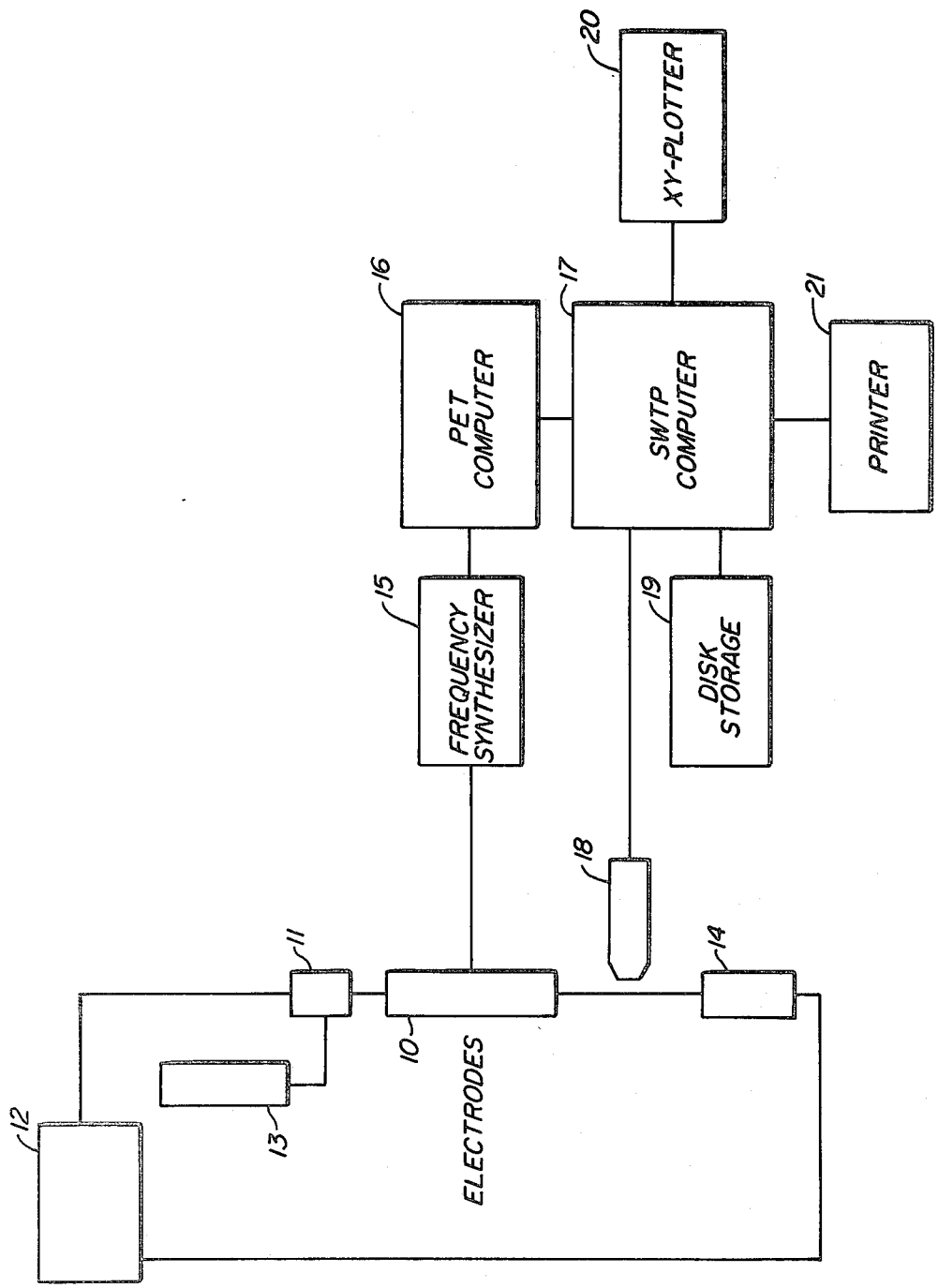
FIG. 1 is a block diagram for one embodiment of circuitry for the particle sorter application of a disk chamber according to the present invention.

Referring to FIG. 1 there is shown a block diagram of a preferred electrical circuit for sorting biological particles. The electrodes to be utilized in the dielectrophoresis process are illustrated by chamber 10. The biological cells are injected into chamber 10 through injector 11 which mixes cells incoming from infusion pump 12 and from the fluid reservoir 13 which provides the fluid in which the cells are suspended. The sorted cells are collected in the stream-splitting means 14. However, in the case of the disk chamber according to the present invention the electrodes 10 also serve as the stream-splitter since the cells are collected in the grooves on the surface of one of the electrodes. Various electrical devices may be utilized to regulate the input frequency and voltage to the electrodes. As shown, the electrodes 10 are regulated by a frequency synthesizer 15, PET computer 16 and SWTP computer 17 which analyzes data observed by television monitor 18. Computer 17 may also be equipped with a disk storage 19, an XY plotter 20 and a printer 21.

Figure 2:
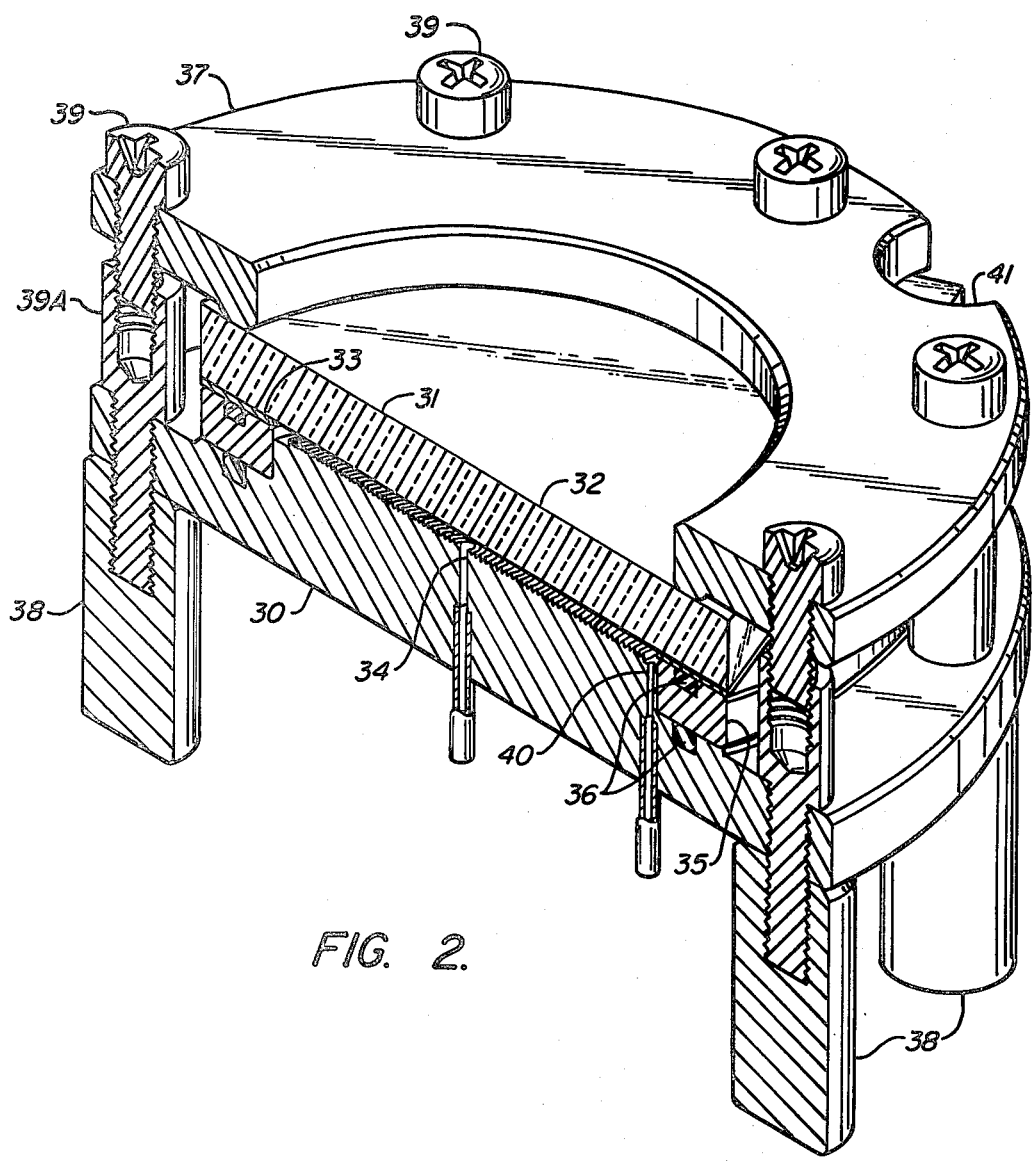
FIG. 2 is a perspective cross-section of a disk chamber embodiment of the present invention.

Referring to FIG. 2 there is shown a perspective cutaway view of a preferred disk chamber cell sorter and cell fuser according to the present invention. Referring to FIG. 2 the disk chamber is defined by lower electrode plate 30 and upper transparent electrode plate 31. Plate 31 is partially coated with conductive layer 33. The electrodes 30 and 31 are parallel and spaced apart at a convenient distance to apply appropriate nonuniform electric fields to cells within the chamber. Typically the spacing between electrodes 30 and 31 will be about 500 micrometers. Electrode 30 has surface 32 into which is cut a plurality of concentric or spirally placed grooves which form sharp edges. The grooves are concentric or approximately concentric about entrance inlet 34. Electrodes 30 and 31 are insulated from each other by insulation ring 35 and insulating O-rings 36. Upper plate assembly 37 is assembled to the lower electrode plate 30 and legs 38 by a plurality of bolts 39 and 39A. Cells which are able to traverse the entire radius within the chamber are collected and withdrawn through exit port 40 and may either be discarded or recycled back into the chamber. The lower electrode 30 may be electrically connected (not shown) to an electrical terminal. The upper electrode 33 may also be connected to an electrical terminal and is accessible to such connection through a cut-out 41 in upper plate 37 which exposes a portion of electrode 31.

Figure 3:
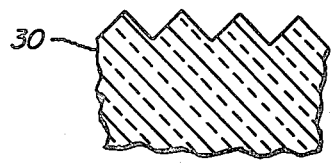
FIG. 3 is an expanded view of the concentric grooved electrode shown in FIG. 2.

Referring to FIG. 3 there is shown an enlarged view of the grooves having sharp points which are cut into the electrode surface of electrode 30.

Figure 4:
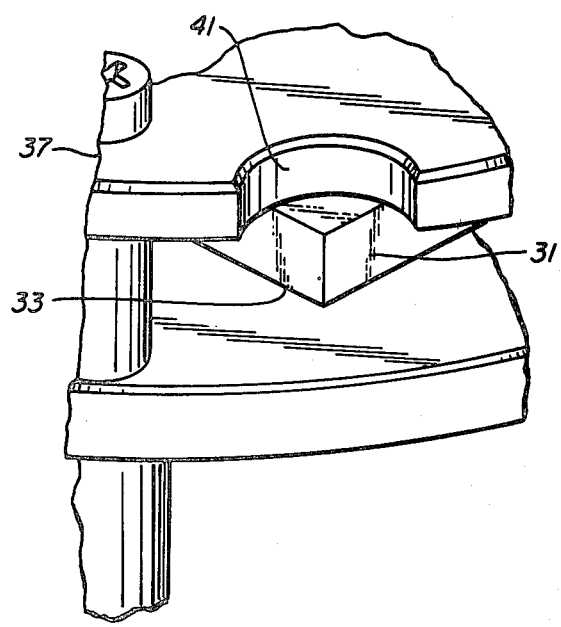
FIG. 4 is a cut-away view of the top plate assembly shown in FIG. 2.

Referring to FIG. 4 there is shown an expanded view of the cut-out 41 in top plate 37 which provides an accessible opening for electrical connection to electrode 31 and conductive undercoating 33. In a typical operation of the apparatus shown in FIG. 2, a stream of biological particles, such as cells, is admitted through port 34 into the chamber defined by electrodes 30 and 31. The biological cells tend to flow, carried by the moving stream, radially and outwardly from the opening in port 34. The frequency and intensity of the ac voltage applied to the electrodes may be varied so that the cells which are desired for collection will arrive at a predetermined radial distance from the opening of port 34, then later collected and withdrawn through exit port 40 when the field is relaxed. The exit port 40 may be connected to a detection device (not shown) which may electronically convert the detection device output signal to a concentration value to provide a measure of the total quantity of cells passing through exit port 40. Exit port 40 may also be connected to a pump means (not shown) for moving the stream of particles through the chamber.

It will be noted that no special treatment of the biological particles prior to sorting is necessary other than to have them suspended in a properly isoosmotic medium of low ionic conductivity. However, the possibility of using special chemicals to modify cellular dielectrophoretic behavior is not precluded and may even be desirable in order to increase the sorting capabilities of the device.

An alternative use of the device shown in FIG. 2 is as an electrofusion device whereby a low ac voltage is applied to electrodes 30 and 31 in order to allow the cells to contiguously align between the electrodes. Typically a mild ac field of about 10 volts rms at about 250 khz may be utilized. Then a brief pulse of about 10 to about 250 volts dc for about 50 microseconds may be applied to cause fusion of the aligned cells. In this manner, a large number of cells may be handled for electrofusion.

It is realized that the frequency, voltage and duration of impulse described above are suggested as typical values, however, it would be within the skill of those of ordinary skill in the art to adjust the various parameters, depending on the type an size of cells which are to be sorted or fused, the type of carrier stream utilized, the type of chemical modification of the cells, if any, which is utilized, and the like.

Figure 5:
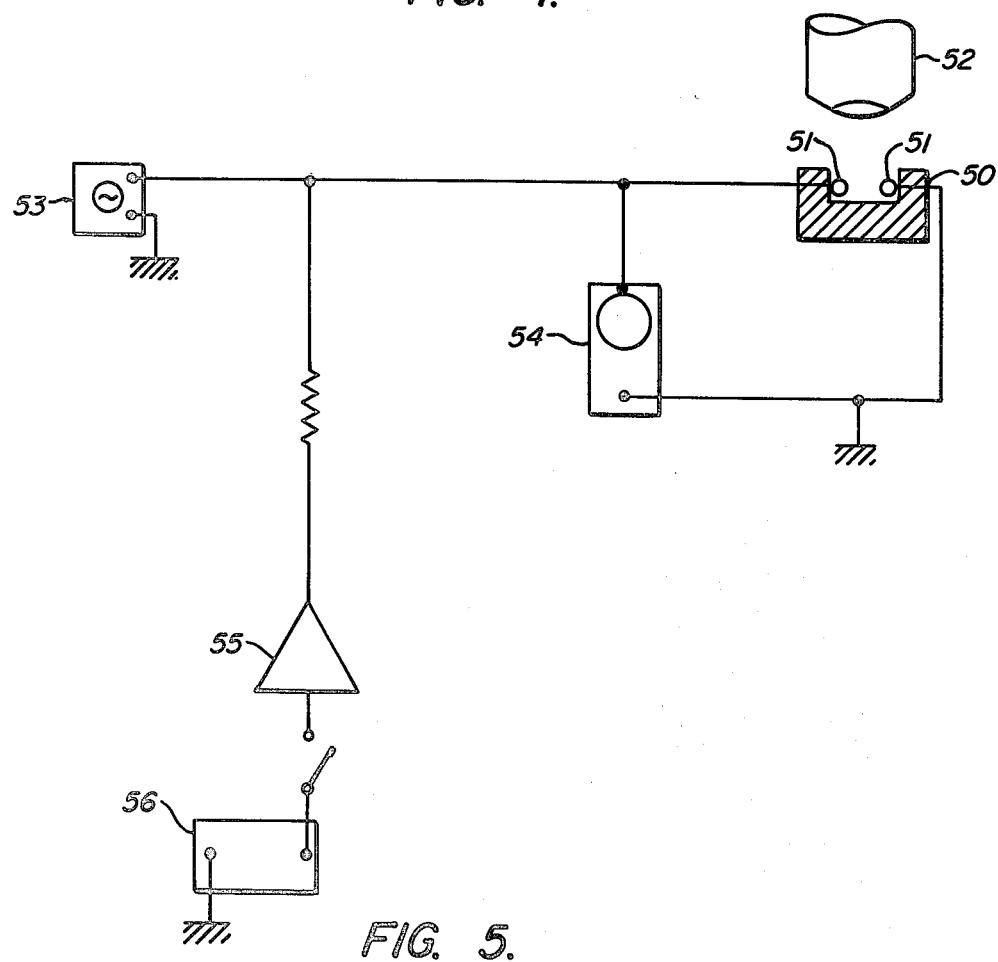
FIG. 5 is a diagram of one embodiment of an electrical circuit for use with a linear chamber fuser according to the present invention.

Referring to FIG. 5 there is shown a diagram of a preferred elecrtrical circuit for utilizing the apparatus of FIG. 2 or a second embodiment according to the present invention, described hereinafter as a linear chamber electrofusion device. The fusion chamber is depicted by 50 and contains parallel electrodes 51. Typically, the course of the electrofusion process may be observed through microscope 52, therefore, it is preferred that at least some of the fusion chamber components be optically transparent. The biological cells within the chamber 50 are first aligned by an ac current provided by oscillator 53 and monitored by oscilloscope 54. Then a short dc pulse is imposed provided by amplifier 55 and conventional commercial stimulator 56.

Figure 6:
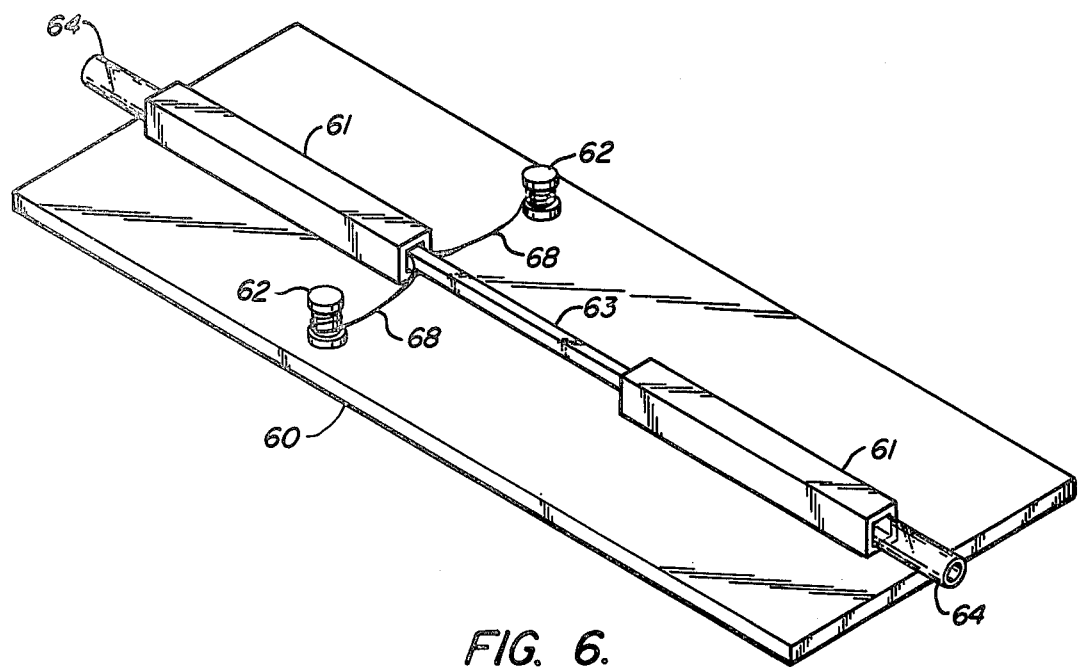
FIG. 6 is a perspective view of a linear chamber fuser according to the present invention.

Referring to FIG. 6 there is shown a perspective view of a preferred linear chamber electrofusion device according to the present invention. Referring to FIG. 6 there is shown an optically transparent base plate 60 which may be, for example, a conventional glass microscope slide. To the base plate 60 is affixed by appropriate adhesive, optically transparent tubular members 61 and metallic electrode terminals 62. Tubular members 61 accommodate optically tranparent linear chamber 63 in which the biological particles are electrofused. The biological particles and fluid support stream are conducted into and out of chamber 63 by inlet and exit means 64, which are preferably stainless steel tubes. Wires 68 connect the electrodes which are located within chamber 63 to terminals 62.

Figure 7:
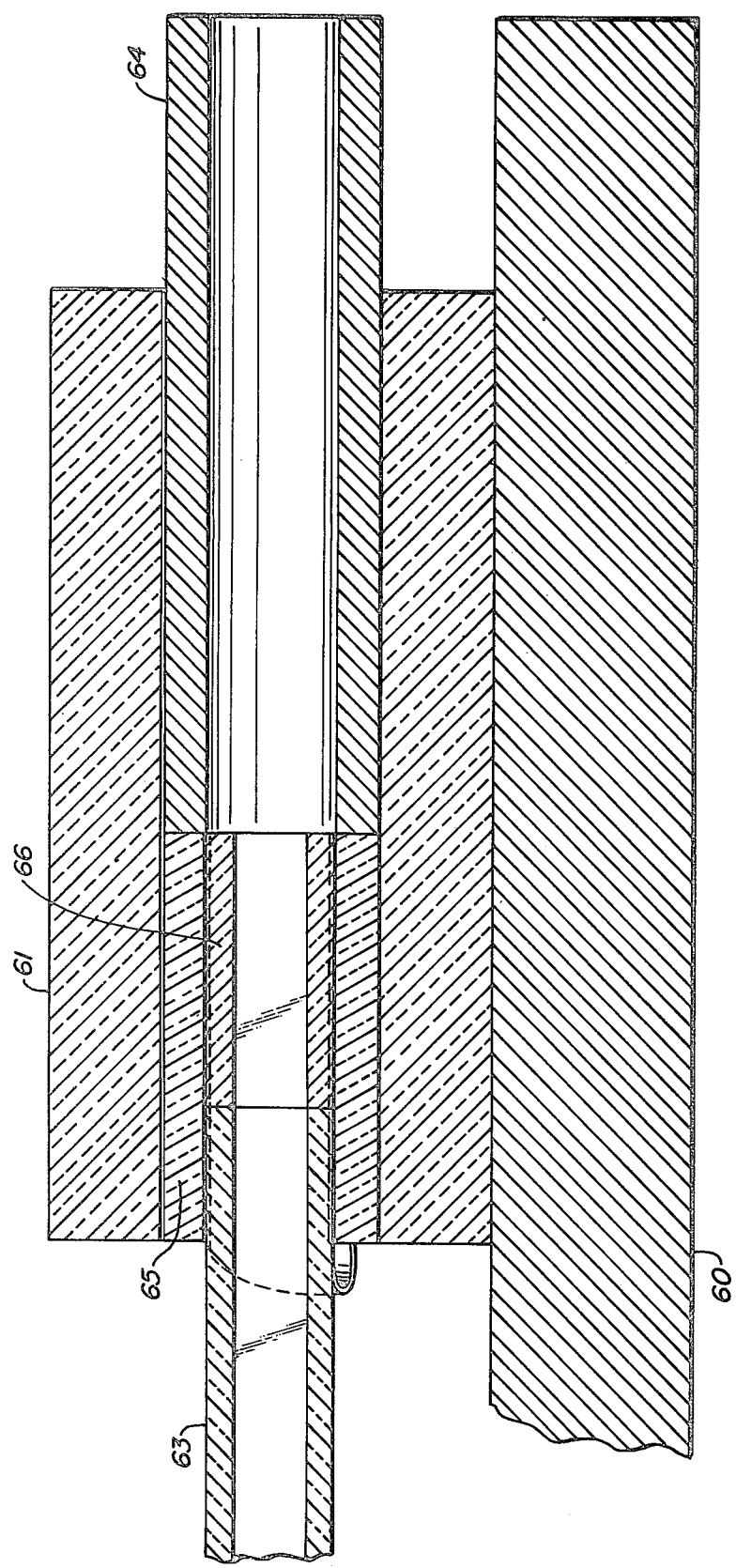
FIG. 7 is an expanded view of a portion of the linear chamber fuser shown in FIG. 6.

Referring to FIG. 7 there is shown an expanded crossectional view of a portion of tubular member 61 accommodating chamber 63 and tube 64. As shown, tubular member 61 is characterized by a longitudinal hole into which are telescoped tube 64 (preferably, stainless steel) and optically transparent sleeve 65 (preferably, glass). Telescoped into sleeve 65 are optically transparent end piece 66 and the end of chamber 63. The central longitudinal orifices of end piece 66 and chamber 63 are of the same height and width. Typically the ratios of the height of the orifice to the width of the orifice will be approximately 10:1. The width of the orifice will be a convenient dimension for accomplishing electrofusion, usually within the range of 200 to 400 microns. The transparent elements 61, 65, 63 and 66 may be conveniently affixed by an appropriate tranparent adhesive. Metallic member 64 may also be affixed by a conventional adhesive, such as epoxy.

Figure 8:
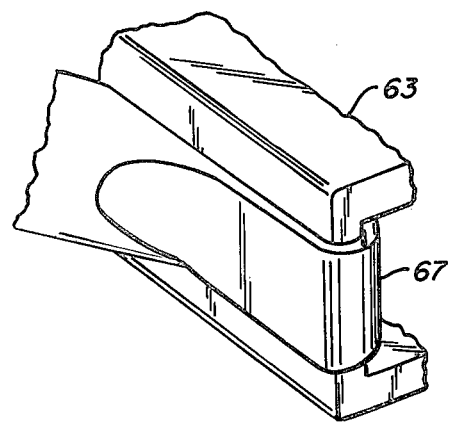
FIG. 8 is an expanded view of the electrode connection to the cell of the linear chamber fuser of FIG. 6.

Referring to FIG. 8 there is shown a partial cutaway of an end of chamber 63 to which one of the electrodes 67 is clipped. The electrodes 67 run along the interior of chamber 63 on oppositely facing walls. The electrodes are long, flat, metallic wires which are flush against facing walls within the chamber 63. At one end of chamber 63 the electrodes 67 are exposed and soldered to wires 68.

In typical operation of the linear electrofusion chamber, the biological cells flow in an appropriately suspending fluid through one of the tubes 64 into chamber 63. The terminals 62 are electrically connected to an ac and dc source as shown in FIG. 5. A mild ac field in the range of about 1 to 20 volts rms, preferably about 10 volts rms, at about 200 to 600 kHz, typically about 250 kHz, is then applied to allow the cells to orient between the electrodes in a contiguous manner to the non-uniform electric field. Then a brief pulse of voltage in the range of 10 to 250 volts dc, typically about 15 volts dc for a period of time in the range of about 1 to 200 microseconds, typically about 50 micro-seconds, is applied and fusion of the cells takes placewithin chamber 63. The fused cells may then be withdrawn through one or both of the tubes 64. The entire electrofusion operation may be observed by placing the slide 60 under a microscope and focusing the chamber 64 for observation. After use, chamber 63 and tubes 64 may be cleaned and sterilized by autoclaving and reused.

It will be appreciated that the foregoing description and specific embodiments are by way of illustration of the particular apparatus described. It will be apparent, however, to those of ordinary skill in the art that many modifications and changes in the specific apparatus may be made without departing from the scope and spirit of the invention.

What is claimed is:

1. A device for fusing neutral polarizable bodies comprising at least two optically transparent elongated tubular members affixed to an optically transparent plate, said members colinearly aligned and spaced apart from each other;

said members accommodating an optically transparent elongated tubular cell, said cell having exterior circumferential dimensions adapted for accommodation by the interior circumferential dimensions of said members, and said cell being of sufficient length such that each end thereof, respectively, extends partially into the openings of said respective members;

two parallel electrodes longitudinally extending along the inner surface of said cell, said electrodes being electrically connected for switching to a direct current or alternating current power source.

2. A device according to claim 1 wherein said members further accommodate means for introducing and withdrawing said particles, respectively, from said cell.

3. A device according to claim 1 wherein said cell is a rectilinear tube having a rectilinear cavity and said electrodes are disposed along opposite walls within said cavity.

4. A device according to claim 3 wherein each said members further accommodates an optically transparent spacer contacting an end of said cell.

* * * * *